United States Patent [19]
Cohen et al.

[11] Patent Number: 5,468,612
[45] Date of Patent: Nov. 21, 1995

[54] 9804 GENE AND METHODS OF USE THEREOF

[75] Inventors: Edward H. Cohen, Somerville; Bryan E. Landgraf, Walpole, both of Mass.

[73] Assignee: Cytomed, Inc., Cambridge, Mass.

[21] Appl. No.: 154,916

[22] Filed: Nov. 19, 1993

[51] Int. Cl.$^6$ .............................. C12Q 1/68; C12N 5/00; C12N 15/00; C07H 17/00
[52] U.S. Cl. .................. 435/6; 435/248.2; 435/320.1; 536/23.5; 935/1; 935/76; 935/77; 935/78; 935/22; 935/24
[58] Field of Search .............................. 435/320.1, 240.2, 435/6; 536/23.5; 935/1, 76–78, 22, 24

[56] References Cited

U.S. PATENT DOCUMENTS 4,946,778  8/1990  Ladner et al. .

FOREIGN PATENT DOCUMENTS 1989-183264  3/1991  Japan .

OTHER PUBLICATIONS

Sommer & Tautz, *Nucleic Acids Research*, vol. 17, No. 16, 1989, p. 6749.
Philbrick et al., Eur. J. Immunol. 1990. 20:87–92.
Baum, C. M., et al., "Isolation of a Candidate Human Hematopoietic Stem–Cell Population", 1992, *Proc. Natl. Acad. Sci.*, vol. 89, pp. 2804–2808.
Chomczynski, P., et al., "Single–Step Method of RNA Isolation by Acid Guanidinium Thiocyanate–Phenol–Chloroform Extraction", 1987, *Analytical Biochem.*, vol. 162, pp. 156–159.
Cohen, J., "Naked DNA Points Way to Vaccines", 1993, *Science*, vol. 259, pp. 1691–1692.
Dumont, F. J., et al., "Interferon–α/β Enhances the Expression of Ly–6 Antigens on T Cells In Vivo and In Vitro", 1986, *Eur. J. Immunol.*, vol. 16, pp. 735–740.
Dumont, F. J., et al., "Selective Up–Regulation by Interferon–γ of Surface Molecules of the Ly–6 Complex in Resting T Cells: the Ly–6A/E and TAP Antigens are Preferentially Enhanced", 1987, *Eur. J. Immunol.*, vol. 17, pp. 1183–1191.
Fleming, T. J., et al., "Characterization of Two Novel Ly–6 Genes", 1993, *J. Immunol.*, vol. 150, pp. 5379–5390.
Gillis, S., et al., "T Cell Growth Factor: Parameters of Production and a Quantitative Microassay for Activity", 1978, *J. Immunol.*, vol. 10, pp. 2027–2032.
Kohler, G., et al., "Derivation of Specific Antibody–Producing Tissue Culture and Tumor Lines by Cell Fusion", 1976, *Eur. J. Immunol.*, vol. 6, pp. 511–519.
Kohler, G., et al., "Fusion Between Immunoglobulin–Secreting and Nonsecreting Myeloma Cell Lines", 1976, *Eur. J. Immunol.*, vol. 6, pp. 292–295.
Kohler, G., et al., "Continuous Cultures of Fused Cells Secreting Antibody of Predefined Specificity", 1975, *Nature*, vol. 256, pp. 495–497.
Kozak, M. "At Least Six Nucleotides Preceding the AUG Initiator Codon Enhance Translation in Mammalian Cells", 1987, *J. Mol. Biol.*, vol. 196, pp. 947–950.
Lin, A. Y., et al., "Expression of T Cell Antigen Receptor Heterodimers in a Lipid–Linked Form", 1990, *Science*, vol. 249, pp. 677–679.
Philbrick, W. M., et al., "The CD59 Antigen is a Structural Homologue of Murine Ly–6 Antigens but Lacks Interferon Inducibility", 1990, *Eur. J. Immunol.*, vol. 20, pp. 87–92.
Raz, E., et al., "Systemic Immunological Effects of Cytokine Genes Injected into Skeletal Muscle", 1993, *Proc. Natl. Acad. Sci. USA*, vol. 90, pp. 4523–4527.

(List continued on next page.)

*Primary Examiner*—W. Gary Jones
*Assistant Examiner*—Bradley L. Sisson
*Attorney, Agent, or Firm*—Fish & Richardson

[57] ABSTRACT

A substantially pure preparation of a 9804 DNA encoding a hematopoietic stem cell protein; antibodies to the 9804 gene product; methods of purifying 9804-expressing cells; and methods of screening for 9804 homologs are disclosed.

5 Claims, 3 Drawing Sheets

OTHER PUBLICATIONS

Rock, K. L., et al., "The LY–6 Locus: A Multigene Family Encoding Phosphatidylinositol–Anchored Membrane Proteins Concerned with T–Cell Activation", 1989, No. 111, pp. 195–224.

Shevach, E. M., et al., "Ly–6: A Multigene Family in Search of a Function", 1989, *Immunol. Today*, vol. 10, pp. 195–200.

Spangrude, G. J., et al., "Purification and Characterization of Mouse Hematopoietic Stem Cells", 1988, *Research Articles*, vol. 241, pp. 58–62.

Spangrude, G. J., et al., "Mouse Hematopoietic Stem Cells", 1991, *Blood*, vol. 78, pp. 1395–1402.

Spangrude, G. J., et al., "Phenotypic Analysis of Mouse Hematopoietic Stem Cells Shows a Thy–1–Negative Subset", 1992, *Blood*, vol. 80, p. 1957–1964.

Stefanova, I., et al., "Characterization of a Broadly Expressed Human Leucocyte Surface Antigen Mem–43 Anchored in Membrane Through Phosphatidylinositol", 1989, *Molec. Immunol.*, vol. 26, pp. 153–161.

Terstappen, L. W. M. M., et al., "Sequential Generations of Hematopoietic Colonies Derived From Single Nonlineage–Committed $CD34^+CD38^-$ Progenitor Cells", 1991, *Blood*, vol. 77, pp. 1218–1227.

Ulmer, J. B., et al., "Heterologous Protection Against Influenza by Injection of DNA Encoding a Viral Protein," 1993, *Science*, vol. 259, pp. 1745–1749.

Van De Rijn, M., et al., "Mouse Hematopoietic Stem–Cell Antigen Sca–1 is a Member of the Ly–6 Antigen Family", 1989, *Proc. Natl. Acad. Sci. USA*, vol. 86, pp. 4634–4638.

Williams, A. F., "Emergence of the Ly–6 Superfamily of GPI–Anchored Molecules", 1991, *Cell Biol. Int'l., Reports*, vol. 15, pp. 769–777.

SEQUENCE LISTING ( 1 ) GENERAL INFORMATION:

( i i i ) NUMBER OF SEQUENCES: 13

( 2 ) INFORMATION FOR SEQ ID NO: 1:

( i ) SEQUENCE CHARACTERISTICS:
( A ) LENGTH: 1066
( B ) TYPE: nucleic acid
( C ) STRANDEDNESS: double
( D ) TOPOLOGY: linear ( x i ) SEQUENCE DESCRIPTION: SEQ ID NO: 1:

```
CAGGACAGGC  TGCTTTGGTT  TGTGACCTCC  AGGCAGGACG  GCCATCCTCT  CCAGAATGAA    60
GATCTTCTTG  CCAGTGCTGC  TGGCTGCCCT  TCTGGGTGTG  GAGCGAGCCA  GCTCGCTGAT   120
GTGCTTCTCC  TGCTTGAACC  AGAAGAGCAA  TCTGTACTGC  CTGAAGCCGA  CCATCTGCTC   180
CGACCAGGAC  AACTACTGCG  TGACTGTGTC  TGCTAGTGCC  GGCATTGGGA  ATCTCGTGAC   240
ATTTGGCCAC  AGCCTGAGCA  AGACCTGTTC  CCCGGCCTGC  CCCATCCCAG  AAGGCGTCAA   300
TGTTGGTGTG  GCTTCCATGG  GCATCAGCTG  CTGCCAGAGC  TTTCTGTGCA  ATTTCAGTGC   360
GGCCGATGGC  GGGCTGCGGG  CAAGCGTCAC  CCTGCTGGGT  GCCGGGCTGC  TGCTGAGCCT   420
GCTGCCGGCC  CTGCTGCGGT  TTGGCCCCTG  ACCGCCAGA   CCCTGTCCCC  CGATCCCCA    480
GCTCAGGAAG  GAAAGCCCAG  CCCTTTCTGG  ATCCCACAGT  GTATGGGAGC  CCCTGACTCC   540
TCACGTGCCT  GATCTGTGCC  CTTGGTCCCA  GGTCAGGCCC  ACCCCTGCA   CCTCCACCTG   600
CCCCAGCCCC  TGCCTCTGCC  CAAGTGGGCC  AGCTGCCCTC  ACTTCTGGGG  TGGATGATGT   660
GACCTTCCTT  GGGGGACTGC  GGAAGGGACG  AGGGTTCCCT  GGAGTCTTAC  GGTCCAACAT   720
CAGACCAAGT  CCCATGGACA  TGCTGACAGG  GTCCCCAGGG  AGACCGTGTC  AGTAGGGATG   780
TGTGCCTGGC  TGTGTACGTG  GGTGTGCAGT  GCACGTGAGA  GCACGTGGCG  GCTTCTGGGG   840
GCCATGTTTG  GGGAGGGAGG  TGTGCCAGCA  GCCTGGAGAG  CCTCAGTCCC  TGTAGCCCCC   900
TGCCCTGGCA  CAGCTGCATG  CACTTCAAGG  GCAGCCTTTG  GGGGTTGGGG  TTTCTGCCAC   960
TTCCGGGTCT  AGGCCCTGCC  CAAATCCAGC  CAGTCCTGCC  CCAGCCCACC  CCCACATTGG  1020
AGCCCTCCTG  CTGCTTTGGT  GCCTCAAATA  AATACAGATG  TCCCCC                  1066
```

( 2 ) INFORMATION FOR SEQ ID NO: 2:

( i ) SEQUENCE CHARACTERISTICS:
        ( A ) LENGTH: 131
        ( B ) TYPE: amino acid
        ( C ) STRANDEDNESS:
        ( D ) TOPOLOGY: linear     ( x i ) SEQUENCE DESCRIPTION: SEQ ID NO: 2:

```
Met  Lys  Ile  Phe  Leu  Pro  Val  Leu  Leu  Ala  Ala  Leu  Leu  Gly  Val  Glu
 1              5                        10                       15
Arg  Ala  Ser  Ser  Leu  Met  Cys  Phe  Ser  Cys  Leu  Asn  Gln  Lys  Ser  Asn
              20                       25                       30
Leu  Tyr  Cys  Leu  Lys  Pro  Thr  Ile  Cys  Ser  Asp  Gln  Asp  Asn  Tyr  Cys
         35                       40                       45
Val  Thr  Val  Ser  Ala  Ser  Ala  Gly  Ile  Gly  Asn  Leu  Val  Thr  Phe  Gly
         50                  55                       60
His  Ser  Leu  Ser  Lys  Thr  Cys  Ser  Pro  Ala  Cys  Pro  Ile  Pro  Glu  Gly
 65                       70                       75                       80
Val  Asn  Val  Gly  Val  Ala  Ser  Met  Gly  Ile  Ser  Cys  Cys  Gln  Ser  Phe
                   85                       90                       95
Leu  Cys  Asn  Phe  Ser  Ala  Ala  Asp  Gly  Gly  Leu  Arg  Ala  Ser  Val  Thr
                  100                      105                      110
Leu  Leu  Gly  Ala  Gly  Leu  Leu  Leu  Ser  Leu  Leu  Pro  Ala  Leu  Leu  Arg
              115                      120                      125
Phe  Gly  Pro
         130
```

( 2 ) INFORMATION FOR SEQ ID NO: 3:

(i) SEQUENCE CHARACTERISTICS:
    (A) LENGTH: 79
    (B) TYPE: amino acid
    (C) STRANDEDNESS:
    (D) TOPOLOGY: linear (xi) SEQUENCE DESCRIPTION: SEQ ID NO: 3:

| Leu | Met | Cys | Phe | Ser | Cys | Leu | Asn | Gln | Lys | Ser | Asn | Leu | Tyr | Cys | Leu |
|---|---|---|---|---|---|---|---|---|---|---|---|---|---|---|---|
| 1 | | | | 5 | | | | | 10 | | | | | 15 | |

| Lys | Pro | Thr | Ile | Cys | Ser | Asp | Gln | Asp | Asn | Tyr | Cys | Val | Thr | Val | Ser |
|---|---|---|---|---|---|---|---|---|---|---|---|---|---|---|---|
| | | | 20 | | | | | 25 | | | | | 30 | | |

| Ala | Ser | Ala | Gly | Ile | Gly | Asn | Leu | Val | Thr | Phe | Gly | His | Ser | Leu | Ser |
|---|---|---|---|---|---|---|---|---|---|---|---|---|---|---|---|
| | | 35 | | | | | 40 | | | | | 45 | | | |

| Lys | Thr | Cys | Ser | Pro | Ala | Cys | Pro | Ile | Pro | Glu | Gly | Val | Asn | Val | Gly |
|---|---|---|---|---|---|---|---|---|---|---|---|---|---|---|---|
| | 50 | | | | | 55 | | | | | 60 | | | | |

| Val | Ala | Ser | Met | Gly | Ile | Ser | Cys | Cys | Gln | Ser | Phe | Leu | Cys | Asn |
|---|---|---|---|---|---|---|---|---|---|---|---|---|---|---|
| 65 | | | | | 70 | | | | | 75 | | | | |

(2) INFORMATION FOR SEQ ID NO: 4:

(i) SEQUENCE CHARACTERISTICS:
        (A) LENGTH: 42
        (B) TYPE: nucleic acid
        (C) STRANDEDNESS: single
        (D) TOPOLOGY: linear     (xi) SEQUENCE DESCRIPTION: SEQ ID NO: 4:

```
GCTCTAGAAG CTTCCACCAT GAAGATCTTC TTGCCAGTGC TG          42
```

(2) INFORMATION FOR SEQ ID NO: 5:

(i) SEQUENCE CHARACTERISTICS:
        (A) LENGTH: 35
        (B) TYPE: nucleic acid
        (C) STRANDEDNESS: single
        (D) TOPOLOGY: linear     (xi) SEQUENCE DESCRIPTION: SEQ ID NO: 5:

```
TAACGGAATT CTCAGGGGCC AAACCGCAGC AGGGC               35
```

(2) INFORMATION FOR SEQ ID NO: 6:

(i) SEQUENCE CHARACTERISTICS:
        (A) LENGTH: 33
        (B) TYPE: nucleic acid
        (C) STRANDEDNESS: single
        (D) TOPOLOGY: linear     (xi) SEQUENCE DESCRIPTION: SEQ ID NO: 6:

```
TAGTAAGAAT TCCTGATGTG CTTCTCCTGC TTG                 33
```

(2) INFORMATION FOR SEQ ID NO: 7:

(i) SEQUENCE CHARACTERISTICS:
        (A) LENGTH: 36
        (B) TYPE: nucleic acid
        (C) STRANDEDNESS: single
        (D) TOPOLOGY: linear     (xi) SEQUENCE DESCRIPTION: SEQ ID NO: 7:

```
TCACTAGAAT TCTCAATTGC ACAGAAAGCT CTGGCA              36
```

(2) INFORMATION FOR SEQ ID NO: 8:

(i) SEQUENCE CHARACTERISTICS:

(A) LENGTH: 79
(B) TYPE: amino acid
(C) STRANDEDNESS:
(D) TOPOLOGY: linear (xi) SEQUENCE DESCRIPTION: SEQ ID NO: 8:

| Leu | Glu | Cys | Tyr | Gln | Cys | Tyr | Gly | Val | Pro | Phe | Glu | Thr | Ser | Cys | Pro |
|---|---|---|---|---|---|---|---|---|---|---|---|---|---|---|---|
| 1 | | | | 5 | | | | | 10 | | | | | 15 | |

| Ser | Ile | Thr | Cys | Pro | Tyr | Arg | Asp | Gly | Val | Cys | Val | Thr | Gln | Glu | Ala |
|---|---|---|---|---|---|---|---|---|---|---|---|---|---|---|---|
| | | | 20 | | | | | 25 | | | | | 30 | | |

| Ala | Val | Ile | Val | Asp | Ser | Gln | Thr | Arg | Lys | Val | Lys | Asn | Asn | Leu | Cys |
|---|---|---|---|---|---|---|---|---|---|---|---|---|---|---|---|
| | | | 35 | | | | | 40 | | | | | 45 | | |

| Leu | Pro | Ile | Cys | Pro | Pro | Asn | Ile | Glu | Ser | Met | Glu | Ile | Leu | Gly | Thr |
|---|---|---|---|---|---|---|---|---|---|---|---|---|---|---|---|
| | 50 | | | | | 55 | | | | | 60 | | | | |

| Lys | Val | Asn | Val | Lys | Thr | Ser | Cys | Cys | Gln | Glu | Asp | Leu | Cys | Asn |
|---|---|---|---|---|---|---|---|---|---|---|---|---|---|---|
| 65 | | | | | 70 | | | | | 75 | | | | |

(2) INFORMATION FOR SEQ ID NO: 9:

(i) SEQUENCE CHARACTERISTICS:
(A) LENGTH: 79
(B) TYPE: amino acid
(C) STRANDEDNESS:
(D) TOPOLOGY: linear (xi) SEQUENCE DESCRIPTION: SEQ ID NO: 9:

| Leu | Glu | Cys | Tyr | Gln | Cys | Tyr | Gly | Val | Pro | Phe | Glu | Thr | Ser | Cys | Pro |
|---|---|---|---|---|---|---|---|---|---|---|---|---|---|---|---|
| 1 | | | | 5 | | | | | 10 | | | | | 15 | |

| Ser | Ile | Thr | Cys | Pro | Tyr | Pro | Asp | Gly | Val | Cys | Val | Thr | Gln | Glu | Ala |
|---|---|---|---|---|---|---|---|---|---|---|---|---|---|---|---|
| | | | 20 | | | | | 25 | | | | | 30 | | |

| Ala | Val | Ile | Val | Gly | Ser | Gln | Thr | Arg | Lys | Val | Lys | Asn | Asn | Leu | Cys |
|---|---|---|---|---|---|---|---|---|---|---|---|---|---|---|---|
| | | | 35 | | | | | 40 | | | | | 45 | | |

| Leu | Pro | Ile | Cys | Pro | Pro | Asn | Ile | Glu | Ser | Met | Glu | Ile | Leu | Gly | Thr |
|---|---|---|---|---|---|---|---|---|---|---|---|---|---|---|---|
| | 50 | | | | | 55 | | | | | 60 | | | | |

| Lys | Val | Asn | Val | Lys | Thr | Ser | Cys | Cys | Gln | Glu | Asp | Leu | Cys | Asn |
|---|---|---|---|---|---|---|---|---|---|---|---|---|---|---|
| 65 | | | | | 70 | | | | | 75 | | | | |

(2) INFORMATION FOR SEQ ID NO: 10:

(i) SEQUENCE CHARACTERISTICS:
(A) LENGTH: 76
(B) TYPE: amino acid
(C) STRANDEDNESS:
(D) TOPOLOGY: linear (xi) SEQUENCE DESCRIPTION: SEQ ID NO: 10:

| Leu | Gln | Cys | Tyr | Glu | Cys | Tyr | Gly | Val | Pro | Ile | Glu | Thr | Ser | Cys | Pro |
|---|---|---|---|---|---|---|---|---|---|---|---|---|---|---|---|
| 1 | | | | 5 | | | | | 10 | | | | | 15 | |

| Ala | Val | Thr | Cys | Arg | Ala | Ser | Asp | Gly | Phe | Cys | Ile | Ala | Gln | Asn | Ile |
|---|---|---|---|---|---|---|---|---|---|---|---|---|---|---|---|
| | | | 20 | | | | | 25 | | | | | 30 | | |

| Glu | Leu | Ile | Glu | Asp | Ser | Gln | Arg | Arg | Lys | Leu | Lys | Thr | Arg | Gln | Cys |
|---|---|---|---|---|---|---|---|---|---|---|---|---|---|---|---|
| | | | 35 | | | | | 40 | | | | | 45 | | |

| Leu | Ser | Phe | Cys | Pro | Ala | Gly | Val | Pro | Ile | Arg | Asp | Pro | Asn | Ile | Arg |
|---|---|---|---|---|---|---|---|---|---|---|---|---|---|---|---|
| | | | 50 | | | | | 55 | | | | | 60 | | |

| Glu | Arg | Thr | Ser | Cys | Cys | Ser | Glu | Asp | Leu | Cys | Asn |
|---|---|---|---|---|---|---|---|---|---|---|---|
| 65 | | | | | 70 | | | | | 75 | |

(2) INFORMATION FOR SEQ ID NO: 11:

(i) SEQUENCE CHARACTERISTICS:
(A) LENGTH: 76

(B) TYPE: amino acid
(C) STRANDEDNESS:
(D) TOPOLOGY: linear (xi) SEQUENCE DESCRIPTION: SEQ ID NO: 11:

| Leu | Gln | Cys | Tyr | Glu | Cys | Tyr | Gly | Val | Pro | Ile | Glu | Thr | Ser | Cys | Pro |
|---|---|---|---|---|---|---|---|---|---|---|---|---|---|---|---|
| 1 | | | | 5 | | | | | 10 | | | | | 15 | |

| Ala | Val | Thr | Cys | Arg | Ala | Ser | Asp | Gly | Phe | Cys | Ile | Ala | Gln | Asn | Ile |
|---|---|---|---|---|---|---|---|---|---|---|---|---|---|---|---|
| | | | 20 | | | | | 25 | | | | | 30 | | |

| Glu | Leu | Ile | Glu | Asp | Ser | Gln | Arg | Arg | Lys | Leu | Lys | Thr | Arg | Gln | Cys |
|---|---|---|---|---|---|---|---|---|---|---|---|---|---|---|---|
| | | 35 | | | | | 40 | | | | | 45 | | | |

| Leu | Ser | Phe | Cys | Pro | Ala | Gly | Val | Pro | Ile | Lys | Asp | Pro | Asn | Ile | Arg |
|---|---|---|---|---|---|---|---|---|---|---|---|---|---|---|---|
| | 50 | | | | | 55 | | | | | 60 | | | | |

| Glu | Arg | Thr | Ser | Cys | Cys | Ser | Glu | Asp | Leu | Cys | Asn |
|---|---|---|---|---|---|---|---|---|---|---|---|
| 65 | | | | | 70 | | | | | 75 | |

(2) INFORMATION FOR SEQ ID NO: 12:

(i) SEQUENCE CHARACTERISTICS:
(A) LENGTH: 79
(B) TYPE: amino acid
(C) STRANDEDNESS:
(D) TOPOLOGY: linear (xi) SEQUENCE DESCRIPTION: SEQ ID NO: 12:

| Leu | Glu | Cys | Tyr | Asn | Cys | Leu | Gly | Val | Ser | Leu | Gly | Ile | Ala | Cys | Lys |
|---|---|---|---|---|---|---|---|---|---|---|---|---|---|---|---|
| 1 | | | | 5 | | | | | 10 | | | | | 15 | |

| Ser | Ile | Thr | Cys | Pro | Tyr | Pro | Asp | Ala | Val | Cys | Ile | Ser | Gln | Gln | Val |
|---|---|---|---|---|---|---|---|---|---|---|---|---|---|---|---|
| | | | 20 | | | | | 25 | | | | | 30 | | |

| Glu | Leu | Ile | Val | Asp | Ser | Gln | Arg | Arg | Lys | Val | Lys | Asn | Lys | Leu | Cys |
|---|---|---|---|---|---|---|---|---|---|---|---|---|---|---|---|
| | | 35 | | | | | 40 | | | | | 45 | | | |

| Phe | Pro | Phe | Cys | Pro | Ala | Asn | Leu | Glu | Asn | Met | Glu | Ile | Leu | Gly | Thr |
|---|---|---|---|---|---|---|---|---|---|---|---|---|---|---|---|
| | 50 | | | | | 55 | | | | | 60 | | | | |

| Thr | Val | Asn | Val | Asn | Thr | Ser | Cys | Cys | Lys | Glu | Asp | Leu | Cys | Asn |
|---|---|---|---|---|---|---|---|---|---|---|---|---|---|---|
| 65 | | | | | 70 | | | | | 75 | | | | |

(2) INFORMATION FOR SEQ ID NO: 13:

(i) SEQUENCE CHARACTERISTICS:
(A) LENGTH: 79
(B) TYPE: amino acid
(C) STRANDEDNESS:
(D) TOPOLOGY: linear (xi) SEQUENCE DESCRIPTION: SEQ ID NO: 13:

| Leu | Glu | Cys | Tyr | Asn | Cys | Ile | Gly | Val | Pro | Pro | Glu | Thr | Ser | Cys | Asn |
|---|---|---|---|---|---|---|---|---|---|---|---|---|---|---|---|
| 1 | | | | 5 | | | | | 10 | | | | | 15 | |

| Thr | Thr | Thr | Cys | Pro | Phe | Ser | Asp | Gly | Phe | Cys | Val | Ala | Leu | Glu | Asp |
|---|---|---|---|---|---|---|---|---|---|---|---|---|---|---|---|
| | | | 20 | | | | | 25 | | | | | 30 | | |

| Arg | Val | Ile | Val | Asp | Ser | His | Arg | Ser | Lys | Val | Lys | Ser | Asn | Leu | Cys |
|---|---|---|---|---|---|---|---|---|---|---|---|---|---|---|---|
| | | 35 | | | | | 40 | | | | | 45 | | | |

| Leu | Pro | Ile | Cys | Pro | Thr | Thr | Leu | Asp | Asn | Thr | Glu | Ile | Thr | Ser | Asn |
|---|---|---|---|---|---|---|---|---|---|---|---|---|---|---|---|
| | 50 | | | | | 55 | | | | | 60 | | | | |

| Ala | Val | Asn | Val | Lys | Thr | Tyr | Cys | Cys | Lys | Glu | Asp | Leu | Cys | Asn |
|---|---|---|---|---|---|---|---|---|---|---|---|---|---|---|
| 65 | | | | | 70 | | | | | 75 | | | | |

9804 GENE AND METHODS OF USE THEREOF

BACKGROUND OF THE INVENTION

The invention relates to the field of hematology and immunology.

Antigens encoded by the murine Ly-6 gene family were originally identified as alloantigens. These antigens are expressed in both hematopoietic and non-hematopoietic tissues (Shevach, E., Immunology Today; Rock et al., 1989 Immunol. Rev. 3:195). The murine Ly-6 locus contains DNA sequences for at least four distinct genes (Fleming, 1993), e.g., Ly-6A, Ly-6C, Ly-F, and Ly6-G, and each gene is characterized by a unique pattern of tissue expression.

Common features shared by members of the murine Ly-6 gene family include: phosphatidylinositolglycan-linkage to the plasma membrane (Williams, A., 1991 Cell Bio. Int Rep, 15:769–777; Rock et al., 1989, Immunol. Rev. 3:195), interferon (IFN) inducibility (Dumont, F. and Coker, L., 1986 Eur. J. Immunol. 16:735–740; Dumont et al. 1987, Eur. J. Immunol. 17:1183–1191), and a predicted protein structure similar to α-bungarotoxin (Fleming et al., 1993, J. Immunol. 150:5379–5390). These proteins also have a characteristic pattern of 8–10 highly conserved cysteine residues and the predicted formation of β-sheet structure. The existence of other proteins which possess similar structural characteristics, yet sharing little DNA sequence homology, may suggest the emergence of a family of structurally-related proteins.

The murine antigen, Sca-1, was first defined on murine bone marrow cells and later shown to be identical to murine Ly-6A.2 (Van de Rijn et alo, 1989, Proc. Natl. Acad. Sci. USA 86:4634–4638). Antibodies to the murine stem cell antigen, Sca-1, have been shown to identify a population of cells enriched in hematopoietic stem cells (Spangrude, G. et al., 1988, Science, 241:58–62; Spangrude, G. et al., 1992 Blood 80:1957–1964).

For human therapy, the isolation of pure hematopoietic stem cells is beneficial for treatments, such as bone marrow transplants. Procedures to isolate pure stem cells are problematic and inefficient due in part to a lack of reliable cell surface markers. Present protocols for isolation of human hematopoietic stem cells rely heavily on stem cell expression of the CD34 antigen (Terstappen et al., 1991, Blood 77:1218–1227) and in some instances by CD34 and Thy-1 expression (Baum, C. M., 1992, Proc. Natl. Acad. Sci. USA 89:2804–2808), however contamination with undesirable cells remains a problem.

SUMMARY OF THE INVENTION

The present invention addresses the difficulty in isolating sufficiently pure human hematopoietic stem cells by providing a novel human hematopoietic stem cell factor, 9804. In one aspect, the invention features a substantially pure preparation of 9804 DNA containing the DNA sequence shown in Table 1 (SEQ ID NO:1) as well as a vector and a cell containing such DNA A "substantially pure DNA", as used herein, refers to a DNA, segment, or fragment which has been purified from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to DNA which has been substantially purified from other components which naturally accompany the nucleic acid, e.g., RNA or DNA, which has been purified from proteins which naturally accompany it in the cell. The invention includes DNA containing the entire sequence of SEQ ID NO:1 as well as DNA fragments containing segments (approximately 8 to 1066 nucleotides) of the sequence of SEQ ID NO:1.

TABLE I

| | | | | | |
|---|---|---|---|---|---|
| CAGGACAGGC | TGCTTTGGTT | TGTGACCTCC | AGGCAGGACG | GCCATCCTCT | CCAGAATGAA |
| GATCTTCTTG | CCAGTGCTGC | TGGCTGCCCT | TCTGGGTGTG | GAGCGAGCCA | GCTCGCTGAT |
| GTGCTTCTCC | TGCTTGAACC | AGAAGAGCAA | TCTGTACTGC | CTGAAGCCGA | CCATCTGCTC |
| CGACCAGGAC | AACTACTGCG | TGACTGTGTC | TGCTAGTGCC | GGCATTGGGA | ATCTCGTGAC |
| ATTTGGCCAC | AGCCTGAGCA | AGACCTGTTC | CCCGGCCTGC | CCCATCCCAG | AAGGCGTCAA |
| TGTTGGTGTG | GCTTCCATGG | GCATCAGCTG | CTGCCAGAGC | TTTCTGTGCA | ATTTCAGTGC |
| GGCCGATGGC | GGGCTGCGGG | CAAGCGTCAC | CCTGCTGGGT | GCOGGGCTGC | TGCTGAGCCT |
| GCTGCCGGCC | CTGCTGCGGT | TTGGCCCCTG | ACCGCCCAGA | CCCTGTCCCC | CGATCCCCCA |
| GCTCAGGAAG | GAAAGCCCAG | CCCTTTCTGG | ATCCCACAGT | GTATGGGAGC | CCCTGACTCC |
| TCACGTGCCT | GATCTGTGCC | CTTGGTCCCA | GGTCAGGCCC | ACCCCCTGCA | CCTCCACCTG |
| CCCCAGCCCC | TGCCTCTGCC | CAAGTGGGCC | AGCTGCCCTC | ACTTCTGGGG | TGGATGATGT |
| GACCTTCCTT | GGGGGACTGC | GGAAGGGACG | AGGGTTCCCT | GGAGTCTTAC | GGTCCAACAT |
| CAGACCAAGT | CCCATGGACA | TGCTGACAGG | GTCCCCAGGG | AGACCGTGTC | AGTAGGGATG |
| TGTGCCTGGC | TGTGTACGTG | GGTGTGCAGT | GCACGTGAGA | GCACGTGGCG | GCTTCTGGGG |
| GCCATGTTTG | GGGAGGGAGG | TGTGCCAGCA | GCCTGGAGAG | CCTCAGTCCC | TGTAGCCCCC |
| TGCCCTGGCA | CAGCTGCATG | CACTTCAAGG | GCAGCCTTTG | GGGGTTGGGG | TTTCTGCCAC |
| TTCCGGGTCT | AGGCCCTGCC | CAAATCCAGC | CAGTCCTGCC | CCAGCCCACC | CCCACATTGG |
| AGCCCTCCTG | CTGCTTTGGT | GCCTCAAATA | AATACAGATG | TCCCCC | (SEQ ID NO: 1) |

In one aspect, the invention includes a DNA which encodes a polypeptide containing the amino acid sequence shown in Table 2 (SEQ ID NO:2). In a preferred embodiment, the invention includes a substantially pure preparation of a polypeptide or a soluble fragment of the polypeptide encoded by the 9804 DNA. As used herein, the term "substantially pure" describes a protein or polypeptide, e.g., a 9804 protein or polypeptide, which has been separated from components which naturally accompany it. Typically, a polypeptide is substantially pure when at least 10%, more preferably at least 20%, more preferably at least 50%, more preferably at least 60%, more preferably at least 75%, more preferably at least 90%, and most preferably at least 99%, of the total material (by wet or dry weight) in a sample is the compound of interest. Purity can be measured by any appropriate method, e.g., in the case of polypeptides by column chromatography, polyacrylamide gel electrophoresis, or HPLC analysis. A substantially purified polypeptide is essentially free of naturally associated components. Polypeptides also include homologous sequences (as defined below); allelic variations; natural mutants; induced mutants; proteins encoded by DNA which hybridizes under high or low stringency conditions to 9804 DNA; and polypeptides or proteins retrieved by antisera raised against a 9804 polypeptide. The invention also provides for other polypeptides, e.g., fusion proteins, which include 9804 polypeptides or fragments thereof. In addition to substantially full-length polypeptides, the present invention provides for soluble fragments of the 9804 polypeptides. As used herein, the term "fragment or segment", as applied to a polypeptide, will ordinarily be at least about 5 contiguous amino acids, typically at least about 10 contiguous amino acids, more typically at least about 20 contiguous amino acids, usually at least about 30 contiguous amino acids, preferably at least about 40 contiguous amino acids, more preferably at least about 50 contiguous amino acids, and most preferably at least about 60 to 80 or more contiguous amino acids in length. Such peptides can be generated by methods known to those skilled in the art, including proteolytic cleavage of the protein, de novo synthesis of the fragment, or genetic engineering.

gene product or a fragment thereof. Preferably, the antibody binds to the 9804 gene product or a fragment thereof and does not substantially recognize and bind to other antigenically-unrelated molecules. Antibodies which bind to 9804 and block 9804 function, e.g., inhibit binding of 9804 to its ligand or prevent signal transduction, as well as those which do not affect 9804 function are included in the invention. Also included in the invention are antibodies which bind to the 9804 gene product in its unmodified as well as post-translationally modified form.

The invention includes not only intact monoclonal or polyclonal antibodies, but also an immunologically-active antibody fragment, e.g., a Fab' or (Fab)$_2$ fragment; an antibody heavy chain, an antibody light chain; a genetically engineered single chain Fv molecule (Ladner et al., U.S. Pat. No. 4,946,778); or a chimeric antibody, e.g., an antibody which contains the binding specificity of a murine antibody, but the remaining portions of which are of human origin.

In another aspect, the invention features a method of

TABLE 2

| Met | Lys | Ile | Phe | Leu | Pro | Val | Leu | Leu | Ala | Ala | Leu | Leu | Gly |
|-----|-----|-----|-----|-----|-----|-----|-----|-----|-----|-----|-----|-----|-----|
| Val | Glu | Arg | Ala | Ser | Ser | Leu | Met | Cys | Phe | Ser | Cys | Leu | Asn |
| Gln | Lys | Ser | Asn | Leu | Tyr | Cys | Leu | Lye | Pro | Thr | Ile | Cys | Ser |
| Asp | Gln | Asp | Asn | Tyr | Cys | Val | Thr | Val | Ser | Ala | Ser | Ala | Gly |
| Ile | Gly | Asn | Leu | Val | Thr | Phe | Gly | His | Ser | Leu | Ser | Lys | Thr |
| Cys | Ser | Pro | Ala | Cys | Pro | Ile | Pro | Glu | Gly | Val | Asn | Val | Gly |
| Val | Ala | Ser | Met | Gly | Ile | Ser | Cys | Cys | Gln | Ser | Phe | Leu | Cus |
| Asn | Phe | Ser | Ala | Ala | Asp | Gly | Gly | Leu | Arg | Ala | Ser | Val | Thr |
| Leu | Leu | Gly | Ala | Gly | Leu | Leu | Leu | Ser | Leu | Leu | Pro | Ala | Leu |
| Leu | Arg | Phe | Gly | Pro | (SEQ ID NO: 2) | | | | | | | | |

The present invention also provides for analogs of the 9804 protein or polypeptide. Analogs can differ from naturally occurring 9804 polypeptide by amino acid sequence differences or by modifications which do not affect sequence, or by both. Analogs may be characterized by alterations in primary amino acid sequence. These peptides include genetic variants, both natural and induced. Induced mutants can be made by various techniques, e.g., by random mutagenesis of DNA encoding the polypeptide using irradiation or exposure to ethanemethylsulfate (EMS), or by site-specific mutagenesis or other techniques known in the art of molecular biology. Also included are analogs which include residues other than naturally occurring L-amino acids, e.g., D-amino acids or non-naturally occurring or synthetic amino acids, e.g., β or γ amino acids. The polypeptides of the invention are not limited to products of any of the specific exemplary process listed herein.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps, e.g., by exposing the polypeptide to enzymes which affect glycosylation e.g., mammalian glycosylating or deglycosylating enzymes. Also embraced are sequence which have phosphorylated amino acid residues, e.g., phosphotyrosine, phosphoserine, or phosphothreonine. Also included are peptides which have been modified so as to improve their resistance to proteolytic degradation or to optimize solubility properties.

In another aspect, the invention includes antibodies, preferably monoclonal antibodies, which are specific for polypeptides encoded by 9804 DNA or fragments thereof. By "specific" is meant an antibody which binds to the 9804 identifying a cell which expresses a 9804 gene product by contacting a population of cells with a 9804-specific antibody and detecting cell-bound antibody. In one embodiment, the 9804-expressing cell is a hematopoietic stem cell. Binding of 9804-specific antibody to a cell indicates that such a cell expresses a 9804 gene product. A "hematopoietic stem cell" is defined as a cell that is capable of developing into a mature myeloid or lymphoid, erythroid cell.

Also provided is a method of purifying a 9804-expressing cell, e.g., a hematopoietic stem cell, by contacting a population of cells with a 9804-specific antibody and collecting cells identified by bound antibody.

The invention also includes a substantially pure DNA consisting essentially of 8 to 1066 nucleotides in the DNA sequence of SEQ ID NO:1. The term "consisting essentially of" as used herein in reference to DNA means that the addition or removal of a few nucleotides (e.g. 2 to 10) to the DNA of the invention has no effect on the ability of the DNA to form a stable hybridization duplex with a homologous DNA. "Homologous," used in reference to nucleic acids, refers to the nucleotide sequence similarity between two nucleic acids. When a nucleotide position in both of the nucleic acids is occupied by the same nucleotide, then they are homologous at that position. The homology between two nucleic acids is a direct function of the number of matching or homologous positions, e.g., if half of the positions in the two nucleic acids are homologous then they are 50% homologous.

In yet another aspect, the invention provides a method of screening for 9804 expression in a cell by contacting the nucleic acid, e.g, DNA or RNA, of a cell with the DNA of the invention and detecting hybridization of the DNA with the nucleic acid. Hybridization under high stringency indicates 9804 expression whereas hybridization under low stringency indicates the expression of a homologous protein.

"Homologous" used in reference to a protein or polypeptide means a protein or polypeptide possessing a pattern of cysteine residues similar to that of the 9804 protein, a glycosylphosphotidylinositol lipid anchor, and nucleotide or amino acid homology of at least 40% and 25% respectively. "High stringency" refers to DNA hybridization and wash conditions characterized by high temperature and low salt concentration, e.g., wash conditions of 65° C. and salt concentration of approximately 0.1×SSC. "Low" to "moderate" stringency refers to DNA hybridization and wash conditions characterized by low temperature and high salt concentration, e.g. wash conditions of less than 60° C. and salt concentration of at least 1.0×SSC.

Unless defined otherwise, all technical terms and scientific terms used herein have the same meaning as commonly understood by one of ordinary skill in the art to which this invention belongs.

Examples of the preferred methods and materials will now be described. These examples are illustrative only and not intended to be limiting as those skilled in the art will understand that methods and materials similar or equivalent to those described herein can be used in the practice or testing of the present invention.

Other features and advantages of the invention will be apparent from the following detailed description, and from the claims.

DETAILED DESCRIPTION

The drawings will first be briefly described.

DRAWINGS

Identification and characterization of the 9804 gene

A novel human cDNA was isolated using a differential screening procedure. The 9804 cDNA encodes a protein with sequence homology to the Ly-6 proteins of the mouse. In particular, an inferred mature 9804 protein, shown in Table 3, shares a 31% amino acid identity with the Ly-6A.2/Ly-6E.1 pair of alleles in the mouse.

TABLE 3

| Leu | Met | Cys | Phe | Ser | Cys | Leu | Asn | Gln | Lye | Ser | Asn | Leu | Tyr |
|---|---|---|---|---|---|---|---|---|---|---|---|---|---|
| Cys | Leu | Lye | Pro | Thr | Ile | Cys | Ser | Asp | Gln | Asp | Asn | Tyr | Cys |
| Val | Thr | Val | Ser | Ala | Ser | Ala | Gly | Ile | Gly | Asn | Leu | Val | Thr |
| Phe | Gly | His | Ser | Leu | Ser | Lye | Thr | Cys | Ser | Pro | Ala | Cys | Pro |
| Ile | Pro | Glu | Gly | Val | Asn | Val | Gly | Val | Ala | Ser | Met | Gly | Ile |
| Ser | Cys | Cys | Gln | Ser | Phe | Leu | Cys | Asn | (SEQ ID NO: 3) | | | | |

The Ly-6A/E locus codes for a hematopoietic stem cell antigen which, in conjunction with some other surface markers, defines a small population of mouse bone marrow cells which are able to fully reconstitute all blood cell lineages in an otherwise lethally irradiated mouse. The 9804 cDNA therefore encodes a human stem cell antigen.

Initial reports on the molecular cloning of the human cell surface antigen, CD59 (Stefanova, I., 1989, Mol. Immunol. 26:153–161), suggested that CD59 may represent the human equivalent of Ly-6. Evidence to the contrary include amino acid sequence comparisons. Human CD59 possesses only an 18 amino acid identity with murine Ly-6A.2 resulting in an overall identity of 23%, whereas an analysis of the predicted amino acid sequence for 9804 gene product and Ly-6A.2 revealed a 25 residue identity resulting in an overall 31% identity. Furthermore, this hypothesis has proven deficient because two important criteria for Ly-6 relatedness, the presence of a multigene family and IFN inducibility, can not be demonstrated with CD59 (Philbrick et al., 1990, Eur. J. Immunol. 20:87–92). Human homologs to the murine Ly-6 genes have not been reported. The difficulty in identifying such homologs may be due to significant divergence in nucleotide sequence among family members.

Analysis of the 9804 gene and amino acid sequence of the inferred mature protein disclosed herein indicate that 9804 is the human homolog of murine Ly-6. The human 9804 cDNA was isolated using a subtractive cloning approach as described below. This DNA can also be used to identify the human equivalents of the mouse Ly-6 family of genes.

General Methods

Standard molecular biology methods were performed as described in Molecular Cloning, Cold Spring Harbor Press, Cold Spring Harbor, N.Y., Ausubel et al., 1993, Current Protocols in Molecular Biology, Green Publishing Associates and Wiley Interscience, New York and Coligan et al., 1993, Current Protocols in Immunology, Green Publishing Associates and Wiley Interscience, New York, with modifications or elaborations as noted below.

Cell Culture

The U-937 human histiocytic lymphoma cell line (ATCC CRL 1593 Rockville, Md.) and peripheral blood lymphocytes (normal, healthy volunteers) were maintained in RPMI-1640 medium supplemented with 10% heat-inactivated fetal bovine serum, 2 mM L-glutamine, 10 mM non-essential amino acids, 10 mM sodium pyruvate, and 50 μM 2-mercaptoethanol. The CTLL-2 indicator cell line (ATCC TIB 214, Rockville, Md.) was also maintained in the above medium further supplemented with 15% conditioned medium from Concanavalin A/phorbol 12-myristate 13-acetate treated rat splenocytes. The COS-7 primate kidney cells (ATCC CRL 1651, Rockville, Md.) were maintained in DMEM medium supplemented with 2 mM L-glutamine, 10% fetal bovine serum, 50 µg/ml penicillin and 50 µg/ml streptomycin.

Subcloning of U-937 cells

U-937 cells were subcloned by plating at a density of approximately 0.1 cell per well in multiple 96-well tissue culture plates. Subcloned cells were then tested in the costimulation assay described below. One subclone, designated subclone 6, was found to be, unlike other clones, only weakly positive in the costimulation assay whereas parental U-937 cells are strongly positive in the costimulation assay.

Transfection of COS-7 cells

Plasmid DNA was transfected into COS-7 cells using Lipofectin or Lipofectamine (Life Technologies, Bethesda, Md.) following the instructions of the manufacturer. Cells were used in the costimulation assay 72 hours after transfection.

Costimulation Assay

Human T cells were purified from the whole blood of healthy donors using T cell Enrichment Columns (R&D Systems, Minneapolis, Minn.) according to the manufacturer's directions. The assessment of costimulatory activity was accomplished by co-culturing the purified T cells with either U-937 cells or COS-7 cells transiently transfected with clone 9804 cDNA ($10^5$/well, each) in a 96-well flat bottomed microtiter tray pre-coated with goat anti-mouse Fab (Sigma, St. Louis, Mo.) at 10 µg/ml. Excess goat anti-mouse Fab was removed by extensively washing the culture wells with phosphate buffered saline prior to the addition of the T cells, U-937 cells, or COS-7 transfectants and 0.1 µg/ml of soluble anti-CD3 (OKT3, Ortho Diagnostics, Raritan, N.J.) Replicates of culture supernatant, harvested after 24 hours, were tested for IL-2 production using the murine CTLL-2 cell line according to published methods (Gillis, S. et al., 1987, J. Immunol. 120:2027–2032). Data were reported as the average of duplicate determinations in units of IL-2 produced (defined as the activity of IL-2 required to elicit half-maximal proliferation of CTLL-2 cells).

Generation of U-937 cDNA library

A cDNA library was made using the vector pCDNAI (Invitrogen, San Diego, Cal.) using procedures known to those skilled in the art. The U-937 cells used as a source of RNA for the making of the library were infected with a Mycoplasma. The library had approximately $1.6 \times 10^6$ independent clones. The library was amplified once, frozen in aliquots and stored at $-70°$ C.

Preparation of total and polyA$^+$ mRNA

Total RNA from cells was prepared using procedures known to those skilled in the art of molecular biology, e.g, the procedures of Chomczynki et al., 1987, Analytical Biochem. 162: 156–159. PolyA$^+$ mRNA was isolated using an mRNA separator kit (Clontech, Palo Alto, Cal.) following the instructions of the manufacturer.

Generation of $^{32}$p radioactively labeled probes

Single stranded cDNA was generated using a cDNA cycle kit (Invitrogen, San Diego, Cal.) following the manufacturer's instructions starting with 1 µg of polyA$^+$ mRNA prepared from subclone 6 cells. $^{32}$p radioactively labeled DNA complementary to the single stranded cDNA was made using a random primed DNA labeling kit (Boehringer Mannheim, Indianapolis, Ind.). The resultant probe was designated probe 1.

A subtracted probe was generated using a Subtractor 1 kit (Invitrogen, San Diego, Cal.) following the manufacturer's instructions. In the terminology used in the instructions, mRNA prepared from subclone 6 cells served as the "uninduced pool of mRNA" and mRNA prepared from U-937 cells served as the "induced pool of mRNA". The subtracted probe, designated probe 2, generated by following kit instructions was enriched for those sequences which were only expressed in the parental U-937 cells or are more highly expressed in the parental U-937 cells than in subclone 6 cells.

All other $^{32}$P labeled probes were prepared from double stranded DNAs using a random primed DNA labeling kit (Boehringer Mannheim, Indianapolis, Ind.).

Screening of U-937 cDNA library

Sample plasmids from the U-937 cDNA library were screened using techniques known to those skilled in art with both the labeled probe synthesized from cDNA made from subclone 6 polyA$^+$ and the subtracted probe. Some of the specific parameters routinely used in the screening process follow. A sample of the library was removed from $-70°$ C. storage, and bacterial colonies from the library grown at approximately 7,000 per 100 mm diameter plate. Routinely 20 such plates were processed at the same time. A nylon filter (Dupont/New England Nuclear, Boston, Mass.) was placed on top of the bacterial colonies on each of the plates. The filter and underlying agar media upon which the colonies were growing were punctured with an 18 gauge syringe needle in six different locations for orientation purposes, and then the filter (designated "type 1") was removed. Most of the bacterial cells from each colony adhered to the filter. Another filter was placed on the original filter, and the two subjected to pressure so that there was a transfer of a portion of each colony from the original filter to the second filter (designated "type 2"). An 18 gauge syringe needle was used to puncture holes in the second filter in positions corresponding to the holes in the first (type 1) filter. The filters were then peeled apart to generate duplicate mirror image surfaces with bacterial cells. The filters were processed per manufacturer's recommendations to bind plasmid DNA from the adhering bacterial cells to the filters. Each plate was returned to a 37° C. incubator for a few hours until the bacterial colonies have regrown and then placed at 4° C. for storage.

All type 1 and type 2 filters were pre-hybridized in CAK solution (5×SSPE, 1% SDS, 0.1% Ficoll, 0.1% polyvinyl pyrrolidone, 0.1% BSA, Torula yeast RNA [Sigma Cat. No. R6625]) at 100 µg/ml for 0.5 to 2 hours at 65° C. Type 1 filters were hybridized with probe 1 at a concentration of $2\times10^6$ cpm/ml of CAK for 16 to 24 hours at 65° C. Type 2 filters were hybridized with the subtracted probe, probe 2, at a concentration of 0.5 to $1.0\times10^6$ cpm/ml of CAK for 16 to 24 hours at 65° C. All filters were then rinsed with 0.1 ×SSC, 0.1% SDS at 65° C. and then washed in 3 changes of 0.1×SSC, 0.1% SDS at 65° C. during the course of approximately 1 hour. Autoradiography was performed on the filters using XAR scientific imaging film (Eastman Kodak, Rochester, N.Y.). X-ray film images of type 1 and type 2 filters were aligned using the orientation holes made in the filters as described above. Regions where the signal from the type 2 filter was stronger than the type 1 filter were identified and colonies picked from the corresponding regions on the plates. Bacteria from colonies picked in the initial screen were rescreened as described above except that the bacterial colonies were kept at a low density (200 or less) on the 100 mm diameter plates. A tertiary rescreening was then done to ensure that a single clone from the library had been purified.

DNA sequencing and DNA analysis

DNA sequences were obtained following procedures known to those skilled in the art. In particular, dideoxynucleotide sequencing was performed using Sequenase Version 2.0 DNA Sequencing kits (United States Biochemical, Cleveland, Ohio) following the manufacturer's instructions. Oligonucleotides used as sequencing primers were either purchased from Invitrogen (San Diego, Cal.) or were custom made by National Biosciences (Plymouth, Minn.).

The compilation and analysis of DNA sequence information was performed using MacVector Sequence Analysis Software version 4.1 (International Biotechnologies/Eastman Kodak, New Haven, Conn.) with ENTREZ Sequences release 5.0, 6.0 or 7.0 (National Center for Biotechnology Information, Bethesda, Md.). In addition, analyses were performed using the e-mail server blast@ ncbi.nlm.nih.gov.

Reversal of 9804 cDNA insert in vector pCDNAI

To reverse the orientation of the 9804 insert with respect to the mammalian enhancer/promoter sequence in the vector pcDNAI for appropriate transcription, DNA from the original 9804 clone was digested with EcoRI restriction endonuclease. This treatment liberated the cloned cDNA as a single fragment via two EcoRI recognition sites, one in each of the two adapter molecules incorporated during the initial generation of the library. The mixture of vector and liberated insert molecules were ligated and transformed into bacteria using techniques known to those skilled in the art of molecular biology. Resultant bacterial colonies were analyzed, and a plasmid with the cDNA insert in the opposite orientation with respect to the original 9804 clone was selected and designated 9804R. The 9804R vector has the pcDNAI mammalian enhancer/promoter in the appropriate orientation for transcription and translation of the 9804 cDNA in mammalian cells.

Generation and subcloning of large and small BstXI restriction fragments

9804 DNA was digested with BstXI restriction endonuclease. Two fragments in addition to the vector molecule are observed because three BstXI restriction sites were present in the DNA containing the 9804 cDNA insert. One BstXI site is present in each of the two adaptor molecules incorporated during the initial generation of the library and one BstXI site is present in the 9804 cDNA itself. The two fragments were blunt ended using $T_4$ DNA polymerase, and each subcloned into blunt ended EcoRV restricted pBluescript II SK+ plasmid DNA (Stratagene, La Jolla, Cal.). These two constructs were used in the DNA sequencing of the 9804 DNA insert. The large fragment subcloned into pBluescript II SK+ was also used for generating random primed $^{32}P$ labeled probe in some experiments.

Polymerase chain reaction (PCR) generation of a truncated version of clone 9804

A truncated version of the 9804 sequence was generated by using a pair of primers in the polymerase chain reaction (PCR). One primer, 5'GCTCTAGAAGCTTCCACCATGAAGATCTTCTTGCCAGTGCTG 3' (SEQ ID NO:4) is a 42-mer which encompasses bases 56 through 79 of SEQ ID NO:1 with the addition of 18 bases (designated by underlining) at the 5' end. These bases encompass the restriction sites XhoI and HindIII as well as place a translational consensus sequence (Kozak, M., 1987, Mo. Biol. 196:947–950) ahead of an ATG. The other primer, 5'TAACGGAATTCTCAGGGGCCAAACCGCAGCAGGGC 3' (SEQ ID NO:5) encompasses the complements of bases 451 through 428 of SEQ ID NO:1 with the addition of 11 bases (designated by underlining) at the 5' end. These underlined bases encompass non-9804 DNA including the restriction site EcoRI. The 425 base pair long PCR product was random primed labeled for use as a probe in Northern analyses.

Cloning of 9804 Kozak consensus fragment into pBJ1-neo vector

Some of the 425 base pair long PCR product was treated with the restriction enzymes, EcoRI and HindIII, followed by treatment with $T_4$ DNA polymerase to create blunt ends. The treated molecules were ligated into EcoRV digested pBJ1-Neo (Lin et al., 1990, Science 249:677–679). The ligated mixture was transformed into bacteria, and plasmids isolated. The two orientations of the insert with respect to the mammalian promoter in the vector pBJ1-Neo were 9804 Kozak consensus-pBJ1-Neo for the correct orientation and 9804 Kozak consensus-pBJ1-Neo-R for the incorrect orientation.

IFN Treatment of U-937 Cells

U-937 cells ($5 \times 10^5$ cells/ml) were incubated in culture medium in the presence or absence of either 100 U/ml INF-γ (Biosource, Carpenteria, Cal.) or 1000 U/ml INF-α (Biosource, Carpenteria, Cal.) for 20 hours. Samples of the cells were washed, collected and analyzed either for HLA class I and class II expression via indirect immunofluorescence or for the expression of message for the cDNA clone 9804 via Northern hybridization techniques described below. Treated cells were also evaluated for their effect on IL-2 production in the T cell costimulation assay.

Northern analyses

Northern analyses were performed on total RNA or polyA+ mRNA following procedures known to those skilled in the art. Human multiple tissue northern (MTN) blots were purchased from Clontech (Palo Alto, Cal.) and processed according to the manufacturer's instructions.

RNA from tissue culture cells or cells obtained from tissue biopsies can be obtained using standard methods, subjected to electrophoreses and blotting onto membrane, e.g., nitrocellulose or hylon, and hybridized with all or part of the 9804 gene as a probe.

Immunofluorescence Staining Techniques

Indirect immunofluorescence staining was performed by incubating appropriately washed cell suspensions ($10^7$ cells/ml, 0.05 ml) at 4° C. for 60 minutes with monoclonal antibodies (2 μg/ml) in phosphate buffered saline, pH 7.4, containing 1% fetal bovine serum and 1 μg/ml rabbit immunoglobulin (Sigma, St. Louis, Mo.). Monoclonal antibody detection employed a secondary FITC-conjugated goat anti-mouse polyclonal antibody titered for optimal reactivity (Calbiochem, San Diego, Cal.). The percentage of antibody reactive cells was determined by flow cytometry.

Molecular Characterization of Clone 9804

One clone, designated 9804, was isolated during the screening of the human U-937 cDNA library on the basis of differential hybridization with two probes. The cDNA insert in the clone was sequenced and found to contain 1066 nucleotides exclusive of a polyA tail of some 81 nucleotides [See Table 1 (SEQ ID NO:1)]. On the basis of Northern analysis, the mature transcript is about 1.3 kb (see FIG. 1).

Ly-6 proteins are compared to the inferred 9804 amino acid sequence in Table 4. Vertical lines are placed above residues in the mouse proteins that retain identity with the 9804 protein and therefore represent an inter-species rather than intraspecies comparison.

There are 10 cysteine residues characteristic of murine Ly-6 genes in the 79 amino acid long sequence (see Table 4). The highly hydrophobic region encompassing amino acids 100 to 131 of SEQ ID NO:2 (see Table 2) is consistent with the processing of the protein into a phosphatidylinositolglycan-linked extracellular membrane protein anchored via the asparagine residue at position 99 of SEQ ID NO:2. The mature protein may be further modified in vivo by glycosylation, phosphorylation, sulfation and other post-translational events.

TABLE 4

A COMPARISON OF HUMAN 9804 PROTEIN SEQUENCE TO MURINE LY-6 SEQUENCES

| PROTEIN | SEQUENCE | |
|---|---|---|
| 9804 | L MC F S C L N Q K S NL Y C L K P T I  CS DQ D N Y C V T V S AS A GI  GN L V T F G H | - SEQ ID NO. 3 |
| Ly-6A.2 | L E C Y Q C Y G V P F E T S C P S I T.  C P Y P D G V C V T.  Q E A A V I  V D S Q T.  R K | - SEQ ID NO. 8 |
| Ly-6E.1 | L E C Y Q C Y G V P F E T S C P S I T.  C P Y P D G V C V T.  Q E A A V I  V G S Q T.  R K | - SEQ ID NO. 9 |
| Ly-6C.1 | L Q C Y E C Y G V P I E T S C P A V T.  C R A S D G F C I A.  Q N I  E L I .  E D S Q R R K | - SEQ ID NO. 10 |
| Ly-6C.2 | L Q C Y E C Y G V P I E T S C P A V T.  C R A S D G F C I A.  Q N I  E L I .  E D S Q R R K | - SEQ ID NO. 11 |
| Ly-6F.1 | L E C Y N C L G V S L GI  A C K S I T.  C P Y P D A V C I S.  Q Q V E L I .  V D S Q R R K | - SEQ ID NO. 12 |
| Ly-6G.1 | L E C Y N CI  G V P P E T S C N T T T.  C P F S D G F C V A.  L E D R V I .  V D S H R S K | - SEQ ID NO. 13 |
| 9804 | S L S K T C S P A C P I P.  E G V N V G V A S M G I . . S C C Q S  F L C N | - SEQ ID NO. 3 |
| Ly-6A.2 | V K N N L C L P I  C P P N I  E S M E I  L G T K V N V K T S  C C Q E D L C N | - SEQ ID NO. 8 |
| Ly-6E.1 | V K N N L C L P I  C P P N I  E S M E I  L G T K V N V K T S  C C Q E D L C N | - SEQ ID NO. 9 |
| Ly-6C.1 | L K T R Q C L S F C P A G V P I  R D P . . . N I  R E R T S  C C S  E D L C N | - SEQ ID NO. 10 |
| Ly-6C.2 | L K T R Q C L S F C P A G V P I  K D P . . . N I  R E R T S  C C S  E D L C N | - SEQ ID NO. 11 |
| Ly-6F.1 | V K N K L C F P F C P A N L E N M E I  L G T T V N V N T S  C C K E D L C N | - SEQ ID NO. 12 |
| Ly-6G.1 | V K S N L C L P I  C P T T L D N T E I  T S N A V N V K T Y C C K E D L C N | - SEQ ID NO. 13 |

Figure 1:
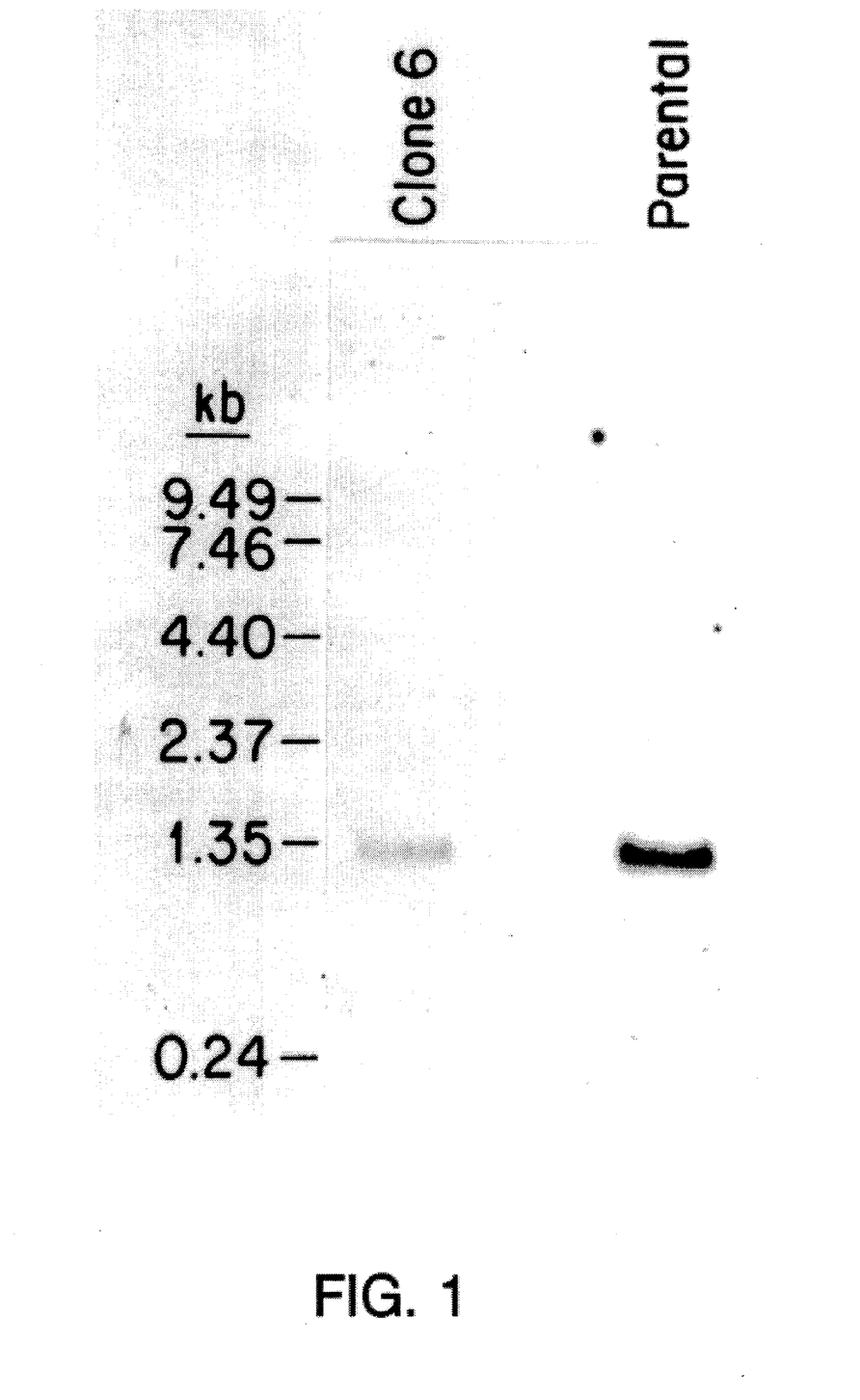
FIG. 1 is an autoradiograph of a Northern blot analysis of polyA⁺ RNA from subclone 6 and parental U-937 cells. 5 μg of polyA⁺ RNA from subclone 6 and U-937 cells were electrophoresed and transferred to nitrocellulose. The large BstXI fragment of the 9804 gene was used as a hybridization probe. The detection of 1.3 kb 9804 homologous transcripts was approximately 5-fold higher in the parental U-937 cells than in subclone 6 cells.
Figure 2:
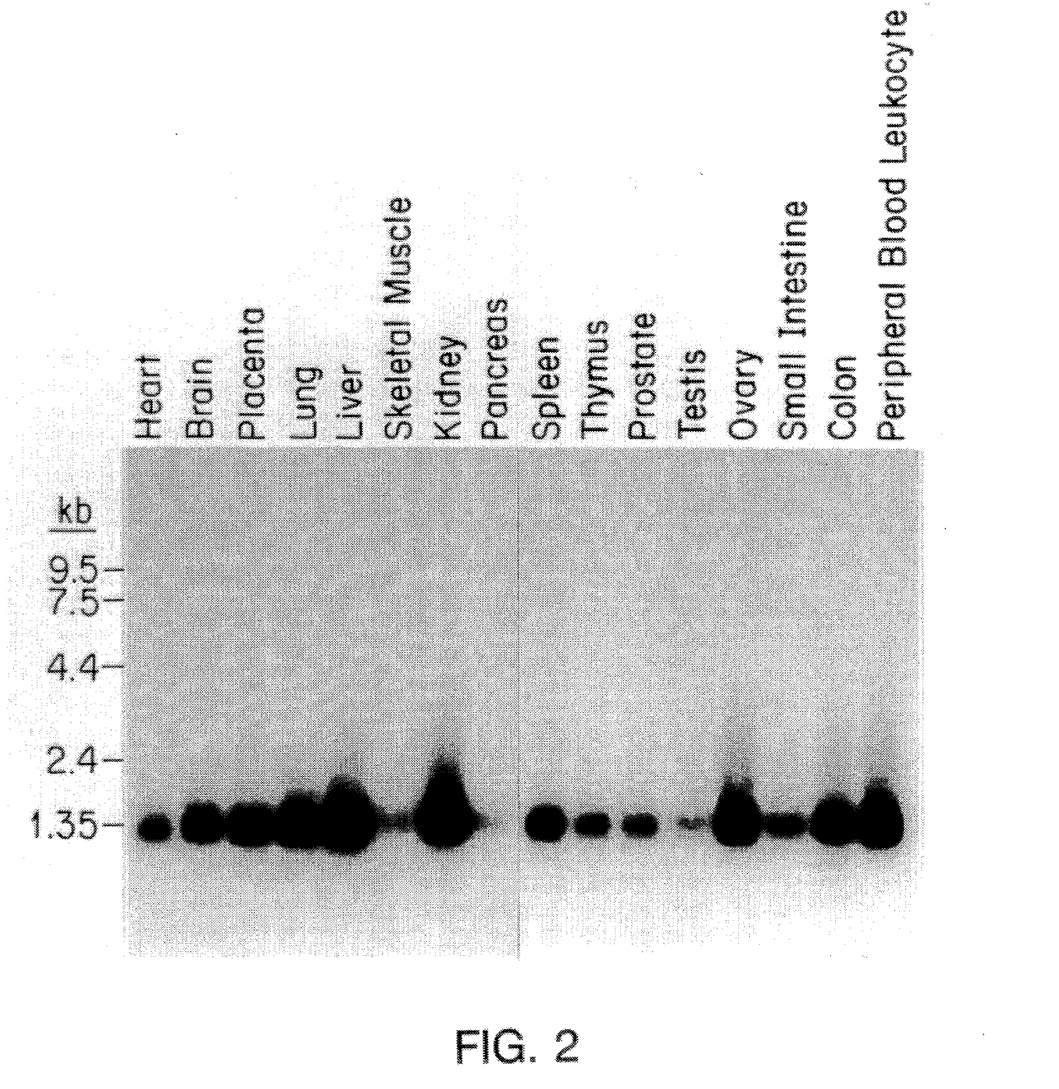
FIG. 2 is an autoradiograph of a Northern blot analysis of polyA⁺ RNA from human tissues. 2 μg of polyA⁺ RNA from each of the noted human tissues was electrophoresed and transferred to nylon membrane. The hybridization probe was 9804 Kozak consensus fragment.

Also shown in FIG. 1, the 9804 gene is more highly expressed in the parental U-937 cells than in subclone 6 cells. A complete 131 amino acid long open reading frame (nucleotides 56 to 448 of SEQ ID NO:1) is contained within the 1066 nucleotide cDNA (SEQ ID NO:1). Employing computer-assisted amino acid sequence analysis, a mature human protein of 79 amino acids with significant homology to amino acid to the murine Ly-6A.2 can be inferred. In particular 9804 protein has 31% amino acid identity with Ly6A.2/LybE.1. The partial amino acid sequences of murine Expression of RNA complementary to clone 9804 in tissues Northern analysis reveals the expression of transcripts homologous with clone 9804 in all human tissues examined (see FIG. 2). The level of hybridization varied and fell into roughly four classes on the basis of relative hybridization signal strength: class 1 (strongest)—liver, kidney, ovary; class 2—brain, placenta, lung, spleen, colon, peripheral blood leukocytes; class 3—heart, thymus, prostate; and class 4 (lowest)—skeletal muscle, pancreas, testis and small intestine. When stringency of wash conditions was increased from 50° C. to 65° C., no change in the relative signal strengths among the various tissues was observed.

Regulation in U-937 cells of sequences homologous with 9804 cDNA

Figure 3:
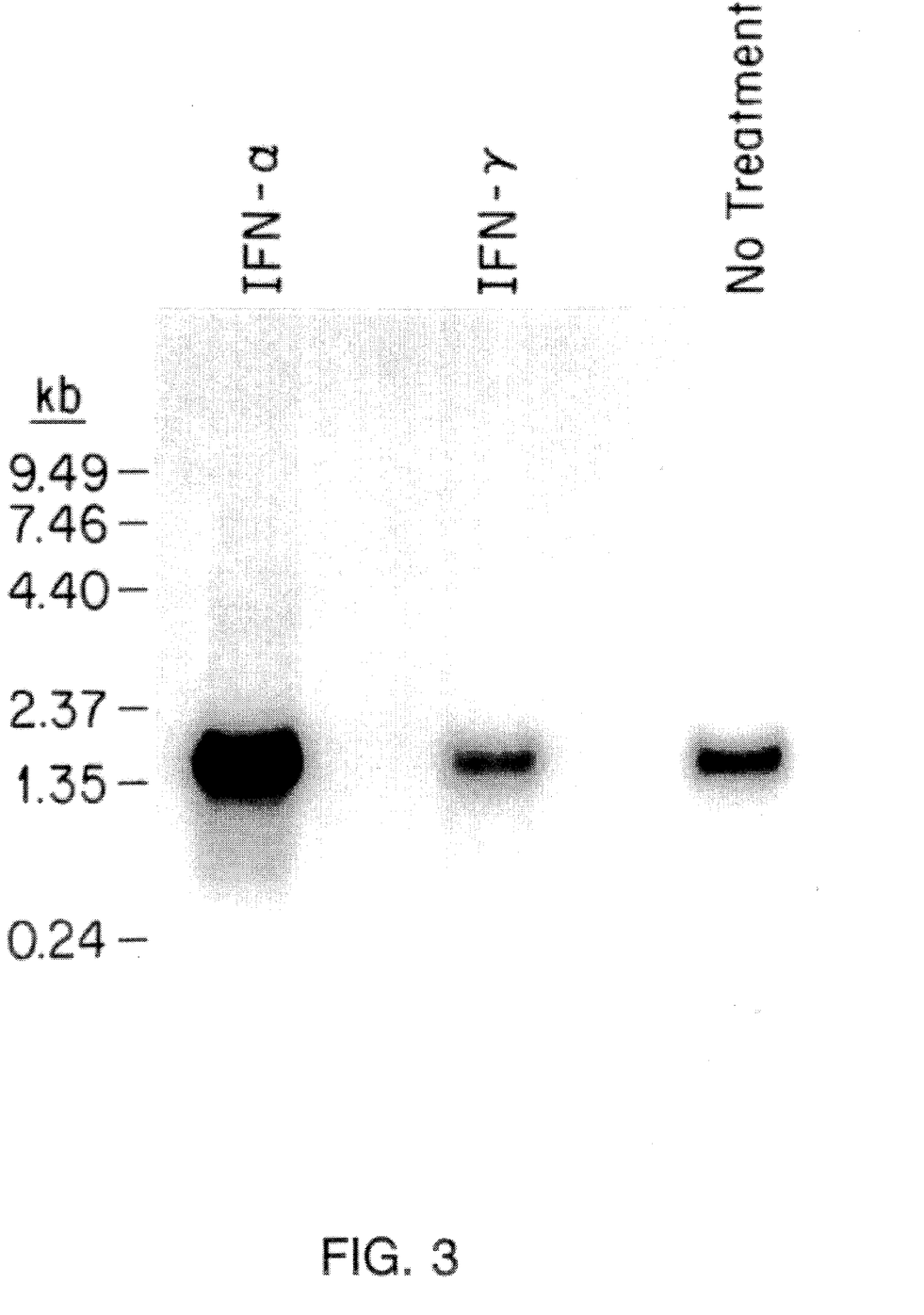
FIG. 3 is an autoradiograph of a Northern blot analysis of RNA from IFN-treated U-937 cells. 10 μg of total cellular RNA from U-937 cells treated with IFN-α, IFN-γ, or no treatment were electrophoresed and transferred to nylon membrane. Hybridization probe was 9804 Kozak consensus fragment. Amount of hybridization of 9804 homologous transcripts was elevated in IFN-α-treated cells with respect to IFN-γ-treated or untreated cells.

Upon treatment of U-937 cells with IFN, an approximately 5-fold increase in the detection of RNA transcripts homologous with 9804 cDNA probe is observed (FIG. 5). This regulation is specific for IFN-α as incubation of the cells with IFN-γ has no effect. These data provide additional evidence for 9804-relatedness to the Ly-6 gene family, and they help to distinguish the 9804 cDNA from CD59, which lacks interferon inducibility.

EXAMPLE 1: Purification of 9804 polypeptide

All or part of the 9804 gene can be engineered into one of many possible protein fusion expression vectors commercially available for the expression and purification of recombinant proteins.

The 9804 protein or polypeptide can be expressed by constructing a fusion protein with maltose binding protein and expressing the hybrid molecule in E. coli. The maltose binding protein fusion and purification system (New England Biolabs, Beverly, Mass.) can be used to overexpress the 9804 gene product by inserting 9804 DNA downstream and in frame of the gene encoding maltose binding protein (malE). In the absence of convenient restriction sites, PCR can be used in order to appropriately modify the cDNA sequence. This well known method can facilitate construction of the recombinant plasmid. Immediately upstream of the insertion site of the pMalE plasmid is a region encoding a factor Xa cleavage site. The presence of this specific proteolytic-sensitive site allows liberation of the cloned protein from the maltose binding protein. Using this expression system, the recombinant protein can be targeted to either the cytoplasm or periplasmic space, depending upon the presence or absence of the malE signal sequence. Purification of the fusion protein can be achieved by passing the crude cell lysate over an amylose resin column, to which the male fusion protein specifically binds. The eluted pure hybrid protein can then be cleaved by factor Xa and the protein of interest purified from maltose binding protein and factor Xa by standard column chromatography.

For example, PCR primers encompassing nucleotides 116 through 136 of SEQ ID NO:1, 5'TAGTAAGAATTCCTGATGTGCTTCTCCTGCTTG3' (SEQ ID NO:6), and complements of nucleotides 352 through 332 of SEQ ID NO:2, 5'TCACTAGAATTCTCAATTGCACAGAAAGCTCTGGCA3' (SEQ ID NO:7) can be used to obtain an appropriate 9804 DNA for subcloning into an expression vector. Non-9804 DNA (designated by underlining), e.g., EcoRI restriction endonuclease recognition sites and spacing nucleotides, were added to the 5' end of each PCR primer. A 9804 DNA fragment of 264 nucleotides can be generated with the PCR primers described above. Following digestion of the 264 nucleotide PCR product with EcoRI, the PCR product is cloned into the EcoRI-digested pMal vectors, pMal-p2 and pMal-c2 bacterial expression vectors. Fusion proteins are expressed and purified according to instructions from the manufacturer, briefly described above. Cleavage by Factor Xa allows for purification of an 83 amino acid polypeptide encompassing 79 amino acids of the 9804 protein.

Alternatively, SDS-polyacrylamide gel electrophoresis can be used to isolate the approximately 9,300 Da protein.

EXAMPLE 2: Anti-9804 antibodies

Antibodies according to the invention may be prepared by a variety of methods well known to those skilled in the art. For example, purified 9804 gene product or antigenic fragments thereof can be administered to an animal in order to induce the production of polyclonal antibodies. Similarly, cells expressing 9804 or antigenic fragments thereof can be used to immunize an animal for production of antibodies. Antibodies according to the invention may also be monoclonal antibodies. Such monoclonal antibodies can be prepared using hybridoma technology (see, e.g., Kohler et al., Nature 256:495, 1975; Kohler et al., Eur. J. Immunol. 6:511, 1976; Kohler et al., Eur J. Immunol. 6:292, 1976; Hammerling et al., In Monoclonal Antibodies and T Cell Hybridomas, Elsevier, N.Y., 1981). Antibodies of the invention include those which are capable of blocking 9804 function, e.g., binding to its ligand or transducing an intracellar signal, as well as those which do not affect 9804 function. Antibodies of each class can be generated by immunization with fragments or functional domains of the 9804 gene product which may be recombinantly made or synthetically produced using a peptide synthesizer. Antibodies which bind to the 9804 gene product in an unmodified form can be generated by immunizing animals with the gene product produced in a prokaryotic cell, e.g., E. coli. Antibodies which bind to a post-translationally modified form, e.g., a glycosylated or phosphorylated protein or polypeptide, can be generated by immunizing animals with gone product produced in a eukaryotic cell, e.g., yeast or insect cell.

A panel of anti-9804 monoclonal antibodies can be produced by hybridizing Sp-2 plasmacytoma cells with splenocytes from a Balb/C mouse repeatedly immunized with purified 9804 polypeptide according to one of the following three methods.

Genetic Immunization

Plasmid DNA containing the 9804 gene sequence and the appropriate promoter regions can be introduced into the hind limb of 6–8 week old female Balb/C mice via intramuscular injection. The injection volume should not exceed 0.05 ml and should contain 50–100 µg of DNA in normal saline. The animals are challenged with three repeat injections every two weeks. Anti-sera can be evaluated for specific reactivity with IFN-α-treated U-937 cells via indirect immunofluorescence and by the ability of the anti-sera to immunoprecipitate in vitro translation products of 9804 cDNA.

Protein Immunization

Recombinant protein produced as described above can be used to immunize animals for the generation of antibodies as follows. The recombinant material can be isolated via affinity chromatography on a maltose column, followed by cleavage with factor Xa. Alternatively, SDS-polyacrylamide gel electrophoresis can be used to isolate the approximately 9 kDa molecular weight protein, whereby the band can be removed from the gel and emulsified with an equal volume of complete Freund's adjuvant. Mice can be intraperitoneally immunized with 50–100 µg of emulsified protein in a total volume of 0.2 ml. After 14 days the animals are hyperimmunized by injection of 50–100 µg/0.2 ml, intraperitoneally using the same immunogen emulsified in incomplete Freund's adjuvant. At least three repeat challenges are performed once every 14 days. The specific reactivity of the anti-sera can be evaluated with IFN-α-treated U-937 cells via indirect immunofluorescence and by the ability of the sera to immunoprecipitate in vitro translation products of 9804 cDNA.

Cellular Immunization

9804 DNA can be co-transfected with the vector pBJ1-Neo into a suitable host cell line, e.g., Balb/c CL.7 cells (ATCC No. TIB 80) or CHO/dhFr⁻ cells (ATCC No. CRL 9096). Alternatively, 9804 Kozak consensus-pBJ1-Neo can be transfected into a suitable host cell line. Transfected cells are initially selected for G418 resistance with further selection being performed using the polyclonal antisera produced from the genetic or recombinant protein immunizations. These sera can screen transfectants for high levels of 9804 expression via immunofluorescence-activated cell sorting. The sorted viable cells can then be expanded, washed in normal saline and intraperitoneally injected ($10^7$ cells/0.5 ml saline) once every two weeks for a total of four administrations. The specific reactivity of the antisera can be evaluated with IFN-α-treated U-937 cells via indirect immunofluorescence and by the ability of the sera to immunoprecipitate in vitro translation products of 9804 cDNA.

Antibody-secreting hybridomas can be produced by the fusion of mouse plasmocytoma cells Sp-2 with splenocytes using the methods well known in the art. Three days prior to fusion, the mouse is boosted again with the immunogen, the isolated spleen cells are then fused with the nonimmunoglobulin producing Sp-2 plasmocytoma cells and cultured in HAT medium. Hybridomas can be screened for the presence of antibodies that either bind to U-937 cells using an $^{125}$I-goat anti-mouse immunoglobulin detection antibody or react with purified recombinant antigen in an indirect ELISA assay. Reactive hybridomas are then subcloned at least twice and culture supernatants prepared for the characterization of antibody specificity, isotype, and binding affinity.

Monoclonal antibodies or fragments thereof can be purified from hybridoma supernatants or ascites fluid using methods known in the art. Murine antibodies can be commercially humanized (Oxford Molecular, Palo Alto, Cal.) or generated using known methods.

In addition to identifying hematopoietic stem cells in a population of bone marrow or other cells, the 9804-specific antibodies can be employed in Western analyses in order to identify recombinant clones expressing the 9804 gene product or 9804 homologs.

EXAMPLE 3: Diagnostic Uses

For diagnostic purposes, 9804 antibodies can be used to identify cells expressing the 9804 protein or polypeptide on their cell surface, e.g., hematopoietic stem cells, using known methods. For example, 9804-specific antibodies can be labeled with a detectable molecule such as fluorescein isothiocyanate (FITC) and allowed to bind to a cell. Cells labeled in this manner can then be detected using a fluorescence microscope or flow cytometer.

In addition to detecting 9804 on the surface of cells, the protein can be analyzed using Western blotting techniques. Cell lysates can be prepared from cultured cells or tissue biopsied from a patient, e.g., bone marrow and solubilized in detergent-containing lysis buffer. The cell extract as well as purified 9804 polypeptide (as a positive control) can then separated by SDS-polyacrylamide gel electrophoresis, followed by transfer to nitrocellulose by electroblotting. To immunologically detect the 9804 polypeptide on the Western blot, a typical antibody binding procedure can be employed, using a known detection protocol, e.g., autoradiography or alkaline phosphatase-based detection. Pre-immune serum or an irrelevant monoclonal antibody can be used as a control for non-specific reactions.

Expression of the 9804 gene product can also be evaluated by analyzing the appearance and amount of 9804 RNA transcripts in a cell using Northern blotting techniques. Regulation of 9804 gene expression can be evaluated by analyzing cellular 9804 gene transcription in response to treatment of the cells with cytokines, e.g., IFN-α, IFN-γ.

Northern blotting with the 9804 DNA and Western blotting with 9804-specific antibodies can be used in tandem to confirm expression of 9804 in a given biological sample.

The 9804 DNA can also be used in Southern blotting assays or in in situ hybridization assays to chromosomally localize the 9804 gene and to perform genetic linkage analysis to localize other genes potentially implicated in disease.

EXAMPLE 4: Therapeutic Uses

Many types of leukemia, lymphoma and other types of immunological disorders or malignancies are treated with bone marrow transplantation. Ideally, patients would be engrafted with a pure population of hematopoietic cells, however, it is presently difficult to obtain such a population of sufficient purity.

The property of self-renewal, multilineage differentiation and rescue of lethally irradiated mice can only be accomplished by true stems cells (Spangrude, G, 1991, Blood 78:1395–1402) and serves as the definitive criteria for their isolation. In the absence of a human Ly-6 equivalent, current methodologies for the isolation of human hematopoietic stem cells are based on the expression of the CD34 antigen (Terstappen LWMM, 1991, Blood 77:1218–1227) and in some instances by expression of CD34 and Thy-1 (Baum, C. M., 1992, Proc. Natl. Acad. Sci. USA 89:2804–2808). The CD34 antigen, while present on human hematopoietic stem cells, is also present on most lineage restricted progenitors in the bone marrow. The selection of $CD34^+$ cells enriches approximately 30–50-fold for the hematopoietic stem cells from normal bone marrow, however, this enrichment does not yield a homogeneous population. Highly purified stem cells are desirable and would be particularly useful in the following situations: 1) the exclusive isolation of stem cells would assist in the removal (purging) of leukemic or solid tumor cell populations from the bone marrow or peripheral blood for autologous bone marrow transplants (BMT) and diminish the potential for graft-versus-host disease (GVHD) in allogeneic BMT, 2) gene therapy applications whereby the efficiency of gene transduction into the stem cell population would be improved by employing more highly purified hematopoietic stem cells, 3) ex vivo culture and expansion protocols for hematopoietic stem cells whereby the total number of input cells can be reduced, thus decreasing the size and cost of these cultures, and 4) expansion of the relevant cells without expansion of the more mature contaminating cell types typically found in current hematopoietic stem cells isolation protocols. The use of positive selection for a cell population based upon the expression of an antigen (i.e., 9804) rather than employing subtle differential selection criteria (i.e., Thy-1$^{lo}$) should be more amenable to incorporation into existing hematopoietic stem cell separation procedures involving solid substrates (plates, columns, resins, or magnetic beads) and eliminate the need for fluorescence activated cell sorting to obtain pure stem cell populations. The discovery of cDNA encoding the protein for the human equivalent of the Ly-6 alloantigens and the production of specific monoclonal antibodies thereof will impact the current approaches toward the isolation of human hematopoietic stem cells. Analogous to murine hematopoietic stem cell purification procedures, antibodies to the human equivalent of the Sca-1 antigen can be used as a tool for the near exclusive isolation of a homogeneous population capable of effecting long term hematopoietic reconstitution.

The invention provides a novel approach to isolate hematopoietic stem cells. The compositions and methods of the invention can be used to isolate a homogeneous population of hematopoietic stem cells of high purity capable of effecting long term hematopoietic reconstitution.

For purification of hematopoietic stems cells to be used for human treatment, e.g., transplantation, bone marrow can be obtained from an HLA-identical or nearly identical donor. Bone marrow cells can then be contacted with the antibodies of the invention alone or in combination with other hematopoietic stem-cell specific antibodies either directly or indirectly labeled with a detectable molecule, e.g., FITC, and fractionated using a process to separate the labeled cells from the unlabeled cells, e.g., flow cytometry. Cells isolated in this manner may be subjected to several rounds of fractionation to achieve a pure population of hematopoietic stem cells suitable for transplantation into human patients.

Nucleic acid probes containing all or part of the 9804 sequence and antibodies which bind to the 9804 gene product can also be used in assays to monitor the effectiveness of therapy, i.e., the reconstitution of a patient's immune system following transplantation of hematopoietic stem cells, by measuring 9804$^+$ cells. A sustained increase in 9804$^+$ cells would indicate successful treatment, whereas no change or a decrease may indicate additional treatment or alternate treatments.

EXAMPLE 5: Screening Methods

Screening for 9804 homologs or proteins closely related to 9804, i.e., members of a gene family, can be identified on the basis of nucleic acid similarities or on the basis of similarities of the expressed protein.

In order to obtain an array of human cDNAs or genomic DNAs related to the 9804 gene, human cDNA or genomic DNA libraries can be screened with DNA probes, e.g., all or part of the 9804 gene radioactively labeled with $^{32}$P, under reduced stringency conditions. cDNA libraries most suitable for screening would be those derived from human bone marrow cells. cDNA libraries derived from other human tissues involved in hematopoiesis or certain human cell lines could also be used for screening purposes. A cDNA library derived from activated T cells could also be used. Methods for construction of cDNA libraries from cells or tissue of interest are well known to those skilled in the art of molecular biology. Alternatively, many such cDNA libraries are commercially available, e.g., from Clontech, Palo Alto, Cal. Such a screening approach can identify nucleic acid sequences which may constitute a family of genes related to 9804. Members of such a gene family can then be utilized as described for 9804 itself.

Screening for 9804 homologs based on nucleic acid similarity can be accomplished as follows. A human bone marrow cDNA library, e.g., Clontech Cat. #HL1168X, (Clontech, Palo Alto, Cal.) can be screened using a random primed DNA probe which encompasses all or part of the 9804 gene sequence, preferably nucleotides encoding the mature 9804 protein [see Table 3, (SEQ ID NO:3)], e.g., nucleotides 116 to 352 of SEQ ID NO:1. Identification of clones with DNA inserts having at least 70% homology with 9804 sequences can be accomplished using hybridization conditions of CAK at 55° C. followed by washes with 0.5× SSC, 0.1% SDS. DNA inserts of clones identified in this manner can be further characterized by DNA restriction endonuclease analysis and DNA sequencing to evaluate similarity to the 9804 gene. Distribution of tissue expression can be analyzed using Northern blotting techniques as described above for 9804.

9804 homologs can also be identified using antibodies raised against the 9804 protein or polypeptide. For example, an expression library derived from cells or tissue, e.g., bone marrow cells, commercially obtained or constructed using known methods, can be screened using standard methods. The library is plated, colonies transferred to a filter, e.g., nitrocellulose, to allow the expressed recombinant protein to bind to the filter. A typical antibody binding and detection protocol (see Example 2) can then be performed using a 9804-specific antibody. DNA inserts from clones identified in this manner can be further characterized by DNA restriction endonuclease analysis and DNA sequencing to evaluate similarity to the 9804 gene. Distribution of tissue expression of the newly identified gene can be analyzed as described above for 9804. Proteins and DNA identified using the screening methods of the invention can be used to detect and purify human cells, e.g., hematopoietic stem cells, for therapy.

What is claimed is:

1. A substantially pure preparation of a 9804 DNA having the sequence of SEQ ID NO:1.

2. A vector comprising the DNA of claim 1.

3. A cell containing the vector of claim 2.

4. A substantially pure DNA encoding a polypeptide which has the amino acid sequence of SEQ ID NO:2.

5. A method of screening for 9804 expression in a cell, which method comprises (a) contacting a gene transcript of a cell with the DNA of claim 5 at a temperature of at least 65° C.; and (b) detecting hybridization of said DNA with said gene transcript, wherein hybridization of said DNA to said gene transcript indicates 9804 expression.

* * * * *

UNITED STATES PATENT AND TRADEMARK OFFICE
CERTIFICATE OF CORRECTION

PATENT NO.   : 5,468,612

DATED        : November 21, 1995

INVENTOR(S)  : Edward H. Cohen and Bryan E. Landgraf

It is certified that error appears in the above-identified patent and that said Letters Patent is hereby corrected as shown below:

On title page, item [56], under "OTHER PUBLICATIONS", column 2, line 8, "Gillis" reference, "vol. 10", should be --vol. 120--;

Col. 2, line 12, after "DNA", insert -- . --;

Cols. 1-2, TABLE 1, column 5, line 7 from the top, replace "GCOGGGCTGC" with --GCCGGGCTGC--;

Cols. 3-4, TABLE 2, column 14, line 7 from the top, replace "Cus" with --Cys--;

Cols. 5-6, TABLE 3, column 3, line 2 from the top, replace "Lye" with --Lys--; TABLE 3, column 7, line 4 from the top, replace "Lye" with --Lys--;

Col. 13, line 44, replace "male" with --malE--;

Col. 14, line 31, replace "gone" with --gene--.

Signed and Sealed this

Twenty-seventh Day of February, 1996

Attest:

BRUCE LEHMAN

*Attesting Officer*    *Commissioner of Patents and Trademarks*